US009915618B2

(12) United States Patent
Mishra et al.

(10) Patent No.: US 9,915,618 B2
(45) Date of Patent: Mar. 13, 2018

(54) METHOD AND AN ARRANGEMENT FOR MEASURING THE GLOSS OF GRAINS

(71) Applicant: Buhler (India) Pvt. Ltd., Attibele (IN)

(72) Inventors: Jyoti Prakash Mishra, Attibele (IN); Bismillah Kani, Attibele (IN); Manit Kumar, Attibele (IN); Gopalakrishnan Trikkur, Attibele (IN)

(73) Assignee: Buhler (India) Pvt. Ltd., Attibele, Bangalore District (IN)

( * ) Notice: Subject to any disclaimer, the term of this patent is extended or adjusted under 35 U.S.C. 154(b) by 0 days.

(21) Appl. No.: 15/108,367

(22) PCT Filed: Feb. 24, 2014

(86) PCT No.: PCT/IN2014/000117
§ 371 (c)(1),
(2) Date: Jun. 27, 2016

(87) PCT Pub. No.: WO2015/102011
PCT Pub. Date: Jul. 9, 2015

(65) Prior Publication Data
US 2016/0320311 A1 Nov. 3, 2016

(30) Foreign Application Priority Data
Dec. 30, 2013 (IN) .......................... 6173/CHE/2013

(51) Int. Cl.
*G01N 21/85* (2006.01)
*G01N 33/10* (2006.01)
*G01N 21/57* (2006.01)

(52) U.S. Cl.
CPC ............. *G01N 21/85* (2013.01); *G01N 21/57* (2013.01); *G01N 33/10* (2013.01); *G01N 2021/8592* (2013.01)

(58) Field of Classification Search
CPC ................... G01N 21/85; G01N 33/10; G01N 2021/8592; G01B 11/303
See application file for complete search history.

(56) References Cited

U.S. PATENT DOCUMENTS 4,285,597 A * 8/1981 Lamprecht ............. G01N 21/57
250/234
5,406,084 A * 4/1995 Tobler .................... G01N 33/10
250/339.01

(Continued)

FOREIGN PATENT DOCUMENTS

| EP | 0 020 971 A1 | 1/1981 |
| EP | 1 046 902 A2 | 10/2000 |
| WO | WO 2009/045035 A1 | 4/2009 |
| WO | WO 2010/125324 A1 | 11/2010 |

OTHER PUBLICATIONS

International Search Report issued by the European Patent Office, acting as the International Searching Authority, for International Application PCT/IN2014/000117 dated Mar. 30, 2015.

*Primary Examiner* — Dominic J Bologna
(74) *Attorney, Agent, or Firm* — Haug Partners LLP

(57) ABSTRACT

The present invention relates to a method and an arrangement for measuring the gloss of grains, in particular rice grains. In one embodiment, the method includes emitting a light beam to the surface of a grain by means of a light emitting device (13), aligning a light sensing device (11) in a sensing position in relation to the light emitting device (13) sensing the light beam of the light emitting device (13) reflected by the surface of the grains in direction of the light sensing device (11), capturing a photometric image of the surface of the grains by means of the light sensing device (11) sensing the reflected light beam, assigning an intensity value to a plurality of image elements of the captured photometric image, wherein the photometric image is composed of the plurality of image elements, quantifying the (Continued)

reflected light beam in predefined ranges of intensities by means of a processing unit, cumulating, for each of the predefined ranges, the number of image elements having an intensity values, within a certain range to density value and assigning to each of the ranges the corresponding density value, capturing a spread value for the density values of the predefined ranges by means of the processing unit, wherein the spread value is captured by measuring the deviation of the density values of the predefined ranges and assigning a quality surface measuring parameter to the captured photometric image, wherein the surface measuring parameter is a measure the spread value.

12 Claims, 2 Drawing Sheets

(56) References Cited

U.S. PATENT DOCUMENTS

| | | | | |
|---|---|---|---|---|
| 5,552,890 | A * | 9/1996 | Nanna | G01N 21/57 101/211 |
| 6,427,128 | B1 * | 7/2002 | Satake | G01N 21/85 209/580 |
| 2006/0256341 | A1 * | 11/2006 | Kuwada | G01N 21/57 356/445 |
| 2007/0153285 | A1 * | 7/2007 | Elton | G01B 11/303 356/446 |
| 2012/0171338 | A1 * | 7/2012 | Hamid | G01N 21/85 426/231 |

* cited by examiner

METHOD AND AN ARRANGEMENT FOR MEASURING THE GLOSS OF GRAINS

CROSS-REFERENCE TO RELATED APPLICATIONS

This application is the National Stage entry under 35 U.S.C. § 371 of International Application No. PCT/IN2014/000117 filed on Feb. 24, 2014, published on Jul. 9, 2015 under publication number WO 2015/102011 A1, which claims the benefit of priority under 35 U.S.C. §119 of Indian Patent Application Number 6173/CHE/2013 filed Dec. 30, 2013.

FIELD OF THE INVENTION

The invention relates to a method for measuring the gloss of grains, in particular rice grains, and it also relates to an arrangement for determining the gloss of grains, in particular rice grains.

BACKGROUND OF THE INVENTION

The specular gloss, respectively shininess, of polished grain or grains, e.g. rice, is an important quality parameter in the grain milling industry. The obtained surface or the luster of the surface of the grain is an expression of the achieved quality of the polishing. The state of the art assessment of the gloss is manually done based on visual measured and therefore subjective to the perception of the assessor. Furthermore a manual assessment of the gloss can be done only batch-wise, in particular random samples, resulting in a not reproducible assessment of the gloss for industrial processed grains.

Generally, it is difficult to judge the quality of grain especially rice which is available in number of varieties which are different in quality, assessed e.g. as high grade or low grade quality. The assessment of quality, e.g. gloss of rice, is determined based on personal judgment which requires at least two samples to be compared. In the absence of any methods that are supported from a scientific view point, the rice thus produced has often tended to be irregular in quality and this has often been the subject of concern.

Gloss is an optical property describing the ability of a surface to reflect light into the specular direction. The factors that affect gloss are the refractive index of the material, the angle of incident light and the surface topography.

Gloss is one of the factors that describe the visual appearance of grains. Grains with smooth surfaces appear glossy. Grains with rough surfaces reflect less specular light and appear dull. Therefore measuring the gloss properties of grains is a method to evaluate the surface quality gloss of the grains.

The appearance of gloss depends on a number of parameters which include the illumination angle, surface condition and observer characteristics.

It is well known to use a gloss meter or similar device for measurement of shininess, which are ideally used for paper, paint and plastics. These meters are typically suited for products with flat surfaces.

In the absence of any defined standards and methods that are supported from a scientific view point, the grain, especially rice, thus produced has often tended to be irregular in quality and this has often been the subject of concern.

It is therefore a need in the art for a method for determining the gloss of grain, especially rice, which can serve as a basis for an objective assessment especially of the quality of polished rice grains.

Furthermore modern plants, in particular rice mills, processing rice grains in large quantities depend on a continuous monitoring of the grain quality, e.g. gloss of the grain. Furthermore a process control to steer the grain plant depending on grains processed would be beneficial to maximize the economic value of the processed grains.

SUMMARY OF THE INVENTION

The present invention provides a method for measuring the gloss of grains, in particular rice grains, by emitting a light beam to the surface of grains by means of a light emitting device. A light sensing device is aligned in a sensing position in relation to the light emitting device, sensing the light beam of the light emitting device reflected by the surface of the grains in direction of the light sensing device. The light sensing device captures a photometric image of the surface of the grains by means of the sensing device by sensing the reflected light beam. To a plurality of image elements of the captured photometric image an intensity value is assigned. The photometric image is composed of the plurality of image elements and the reflected light beam is quantified in predefined ranges of intensities by means of a processing unit. Cumulate, for each of the predefined ranges, and assigning to each of the ranges the corresponding density value and capture a spread value for the density values of the predefined ranges by means of the processing unit. The spread value is captured by measuring the deviation of the density values of the predefined ranges. A quality surface measuring parameter is assigned to the captured photometric image, wherein the surface measuring parameter is a measure the spread value.

Preferably there is based on the measured surface measuring parameter an output signal based on the measured surface measuring parameter is generated, wherein the output signal is useable for steering one or more process steps of a grain mill processing the grains.

Preferably the spread value is a measure of the dispersion/deviation of the density values of the predefined ranges of the captured image from an average image element density value also mentioned as standard deviation.

Preferably the light sensing device is a photometer, digital camera or photometric sensor.

Preferably the photometric image is fragmented in a plurality of image elements, i.e. pixels.

Preferably the method further comprises triggering for image elements with intensity values within a certain range and assigning a density value to each of the predefined ranges of intensities, wherein the density value correspond to the cumulated number of image elements having intensity values within the certain range.

Preferably the reflected light of the light emitting device at the surface of the grains under the given angle provides information on the reflection properties, i.e. the quality of the surface of the grains i.e. the specular gloss or shininess, of the surface of the grain.

Gloss is a term used to define an optical property of a surface to reflect light in a specular direction. The factors that affect gloss are the refractive index of the material, the angle of incident light and the surface topography. Therefore with the measurement of reflection of light on the grain under a given angle it is possible to assess the surface topography, e.g. shine, of the grain.

The captured photometric images are then processed by the processing unit an image processing algorithm and the spread value determine the degree of gloss. The higher the spread value, the more is the degree of gloss. That means a higher deviation, e.g. standard deviation, signifies a higher degree of gloss. The standard deviation is used therein to show how much variation or dispersion from the average (mean) pixel intensity exists. A low standard deviation indicates that the intensity of the pixels in the photometric image tends to be very close to the mean and a high standard deviation indicates that the intensity of the pixels in the photometric image is spread out over a large range of values. The standard deviation has the advantage that it is algebraically simple and therefore little computing capacity of the processing unit is necessary for a processing of the photometric image. Using the average absolute deviation, that is the average of the absolute deviations, has the advantage that it is a very robust method. For conveying the sample of grains to the measuring portion a channel, e.g. tube, may be provided having a transparent window, to allow the light sensing device, i.e. a digital camera, to take the picture of the grain from outside the channel.

According to an embodiment several photometric images are captured. That can help to come to an even more reliable result of assessment of the surface quality of the grains, i.e. the gloss of the grains, especially the rice. If the light emitting device and the light sensing device are shifted relative to each other and/or relative to the position of the grains different situations respecting light reflected from the surface of the grains can be achieved. If this photometric images are analyzed each for its own or analyzed in combination with each other this can lead to an even more significant result with respect to gloss of the grain. Using several photometric images with different positions of the light sensing device or the light emitting device relative to the measured grains allows to access the gloss by analyzing the change in specular reflection as the specular angle changes. In this invention, the light emitting device, i.e. the camera and light sensing device are placed at specified angles. They are not relatively shifted. All images are captured at the same specified angles According to the present embodiment the photometric image is a digital monochrome image.

Another embodiment of the photometric image is a color image. The standard deviation is performed for at least one color channel, e.g. the red and/or green and/or blue channel of an RGB image.

In the present embodiment the deviation is performed of a grayscale photometric image. For some kind of gloss properties of grain the light reflecting properties of the grain depend on the wavelength of the light that is to be reflected or rather emitted from the grain. So meet this effect it can be implemented in the method according to the present invention to either light the grain with light in some definite limited wavelength range or to filter the image to extract or delete wavelengths. One embodiment to filter the image is by using selective light sensing device or algorithm performed by the processing unit. Another embodiment to filter the photometric image is a special light emitting device emitting light only in a restricted range of wavelength. It is possible, too to have the light emitting device provided with a light filter for filtering out some light wavelengths. Preferably the light emitting device comprises a white LED as a light emitting mean and no specific wavelengths or filters are used.

According to an embodiment the standard deviation of at least two color channels of images are combined to determine the degree of gloss. Sometimes the extraction of pixel intensities and their deviation of different colors provide more significant information on the degree of gloss of the grain. These photometric images for the different colors can also be taken at different times or from different angles, e.g. with separate light sensing devices, i.e. cameras, for the colors to have optimal picture taking angles for each color.

According to an embodiment in the step of acquiring the image at least one light emitting device is placed to spot light on the grain at the shine measurement zone that is reflected from the grain to the light sensing device, i.e. camera. The additional light emitting device improves the given light situation. The color of the light can be varied by the provided light emitting device itself or filters at the light emitting device. The angle of illumination of the grains can be chosen in putting the light emitting device at a selected place. Further the light can be synchronized with the light sensing device. A flashlight can be used to provide bright high-contrast light only when it is needed.

According to an embodiment at the center of the shine measurement zone the direction to the light sensing device, i.e. camera, and the direction to the light emitting device comprise an angle of 120° to 150°. It has been found out in a series of experiments that an optimal photometric image is achievable when the light emitting device is arranged opposite the light sensing device, i.e. camera, so that the light is radiated from the light emitting device under a relative sharp angle on the grains and from the grain reflected or emitted to the light sensing device, i.e. camera. The grain functions thereby as a kind of mirror. Therefore the light sensing device, i.e. camera is oriented e.g. at an angle of 15° to 30° to a conveying direction of the grain sample at the measuring portion and the light emitting device is oriented e.g. at an angle of 5° to 20° to the conveying direction. This allows to realize the angle range of 130° to 160°.

According to an embodiment the sample grain is conveyed during acquiring the photometric images. When the grain is conveyed while acquiring the image, it is possible to achieve a constant measurement of gloss, e.g. online after a polishing step of the grain in a grain plant. Thus, neither the conveying system needs to be stopped for acquiring the photometric image, nor grain has to be led out of the conveying system for getting the photometric image. The grain logistic capacity can therefore kept high during measurement of gloss and assessment of grain quality.

According to an aspect the present invention provides an arrangement for determining the gloss of grain, the arrangement comprising: a channel for supplying grain, a light emitting device for radiating light on the grain, and an light sensing device to capture an image of the grain, wherein further an image processing unit is provided to generate a histogram showing the number of pixels in an image at each different intensity values found in that image, to calculate a deviation from the histogram, and to determine the degree of gloss of the grain based on the calculated deviation. At the center of the shine measurement zone the direction to the camera and the direction to the light emitting device comprise e.g. an angle of 130° to 160°. The light sensing device, i.e. camera is e.g. oriented at an angle of 15° to 30° to the conveying direction and the light emitting device is e.g. oriented at an angle of 5° to 20° to the conveying direction.

According to an embodiment a mirror is provided to reflect light emitted from the light emitting device from the grain sample to the light sensing device. e.g. camera or to reflect light from the light emitting device to the grain sample. By this measure flexibility with regard to the positioning of the light relative to the light sensing device can be achieved. The light sensing device can be positioned beside the light emitting device and the mirror opposite to them. The light shines then first from the light emitting device on the grain. From the grain the reflected or emitted light shines then on the mirror from which it is mirrored back to the light sensing device, e.g. camera. The light sensing device and the light can thereby also be built as one unit with a power supply. This can help to simplify the arrangement.

The method and arrangement for determining the gloss of grain according to the present invention allow it to quantify the gloss, respectively shininess, of grain by an innovative optical arrangement. The manual process of accessing the grain done by a grain miller can be replaced. The method and arrangement provide a more objective and accurate measurement of the gloss effect. Further, the new method can offer a continuously monitoring of the grain quality without affecting the grain conveying. The method and arrangement provide a quantifying of the gloss in form of a numerical value. That makes it easier to transmit information on the grain quality, especially the gloss. The arrangement is intended to be part of a grain polishing system or situated downstream of the polishing system in the grain conveyance. The operator of the grain polishing system is helped taking quick decisions using actual quality information on the grain. Thus, the grain quality can be improved. Furthermore the output signal is useable as a steering signal for a control unit of a grain mill plant.

BRIEF DESCRIPTION OF THE DRAWINGS

The above and other aspects, features, and advantages of certain exemplary embodiments of the present invention will be more apparent from the following description taken in conjunction with the accompanying drawings in which.

Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure.

Throughout the drawings, it should be noted that like reference numbers are used to depict the same or similar elements, features, and structures.

DETAIL DESCRIPTION OF THE DRAWINGS

Figure 1:
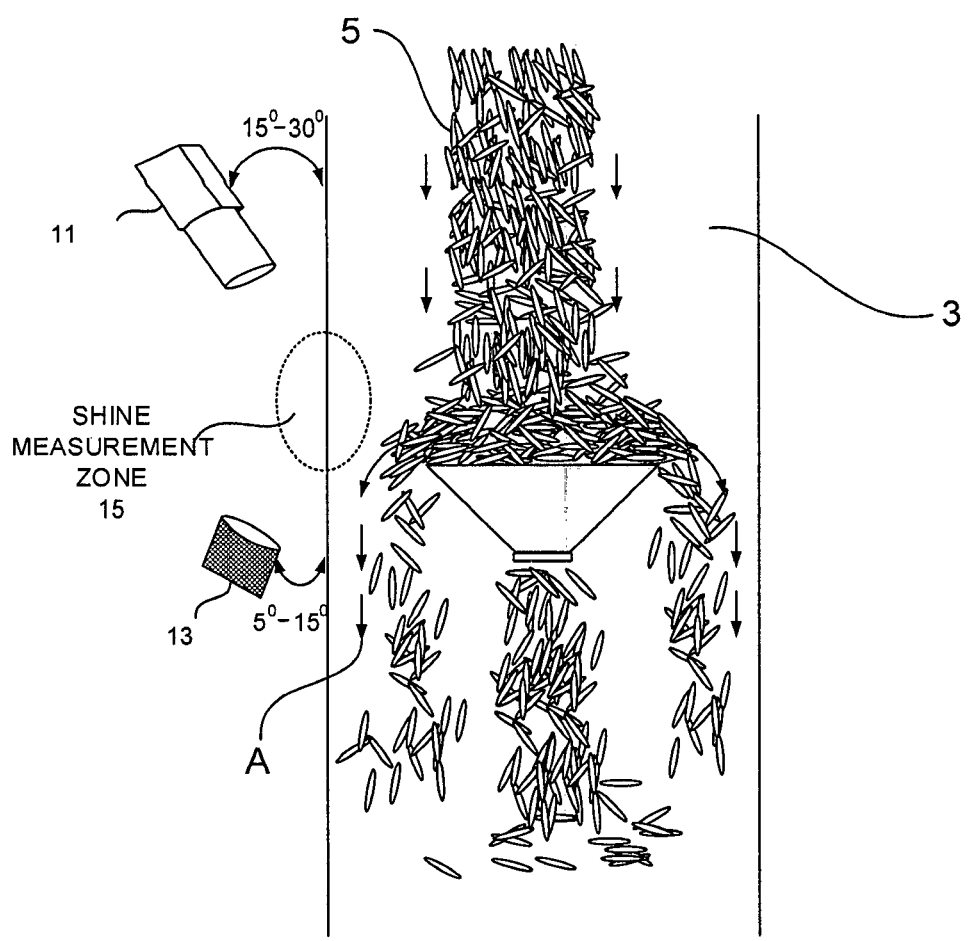
FIG. 1 is a schematic view showing an arrangement for determining the gloss of grain according to a first embodiment of the invention.

FIG. 1 is a schematic view showing an arrangement 1 for determining the gloss of grain 5 according to a first embodiment. A channel 3 is illustrated in FIG. 1 having a vertical orientation. Grain 5 is conveyed through the channel 3. A conveying direction of the grain 5 is illustrated by arrows A. The conveying direction A is illustrated downward, others orientations are possible. The channel 3 can be realized as bypass of a main conveying channel for the grain 5. This allows providing special flow conditions of the grain 5 in the channel 3 which are adapted for measuring the gloss, respectively shininess, of the grain 5. So it is possible to have a slower grain 5 transportation velocity in the channel 3 than in the main channel or to stop conveying the grain 5 in the channel 3 for a short time for capturing an image of the grain 5.

A light sensing device 11, realized as digital camera in this embodiment, is provided focusing on the grain 5 in the channel 3 for acquiring an image of the grain 5. In this embodiment the light sensing device 11 is located outside the channel 3. The light sensing device 11 is directed on the grain 5 in a shine measurement zone 15 provided at the channel 3 in this first embodiment. The shine measurement zone 15 is build transparent to allow the light sensing device 11 acquiring an image of the grain 5 inside the channel 3. The light sensing device 11 is oriented focusing in a direction under an angle $\alpha$ of 15° to 30° to the direction of the grain flow A in the shine measurement zone 15.

A light emitting device 13 is provided focusing on the grain 5 in the channel 3 for improving the light conditions for acquiring the image of the grain 5. In this embodiment the light emitting device 13 is located outside the channel 3. The light emitting device 13 is directed on the grain 5 in the shine measurement zone 15. The light emitting device 13 is oriented focusing in a direction inclined under an angle $\beta$ of 5° to 15° to the direction of the grain flow A in the shine measurement zone 15. Thus, the focusing direction of the light sensing device 11 is directed towards the focusing direction of the light emitting device 13, whereby the focusing directions cross at or are inclined under an angle of 130° to 160°.

Light is cast by the light emitting device 13 on the grain 5 in the shine measurement zone 15 and reflected, respectively emitted, from there towards the light sensing device 11. The reflected, respectively emitted light, coming from the grain 5 and resulting from the light emitting device 13 is captured in the image made by the image acquiring device 11 and used for accessing the degree of gloss, respectively shininess, of the grain 5.

The reflection of the light of the light emitting device 13 at the surface of the grain 5 under the given angle provides information on the reflection properties, i.e. the gloss or shininess, of the surface of the grain 5. The reflected light is captured on the image by the light sensing device 11.

Two components are mainly responsible for the appearance of gloss, namely specular reflection (the main component which is the amount of light reflected from a surface in an equal and opposite direction to the angle of light striking it) and diffuse reflection (the amount of light that is scattered over a range of directions). A surface with more specular reflection has a high gloss and a surface has less gloss, when light is reflected more diffuse from there.

Of special interest with respect to the assessment of specular gloss of the grain 5 is therefore the distribution of brightness, i.e. intensity of pixels, of areas in the image resulting from reflection of light cast from the light emitting device 13 on the grain 5.

Therefore the image acquiring device 11 comprises or is connected to an image processing unit to generating a histogram showing the number of pixels in an image at each different intensity values found in that image, to calculate a deviation from the histogram, especially the standard deviation or average absolute deviation, and to determine the degree of gloss of the grain 5 based on the calculated deviation.

Figure 2:
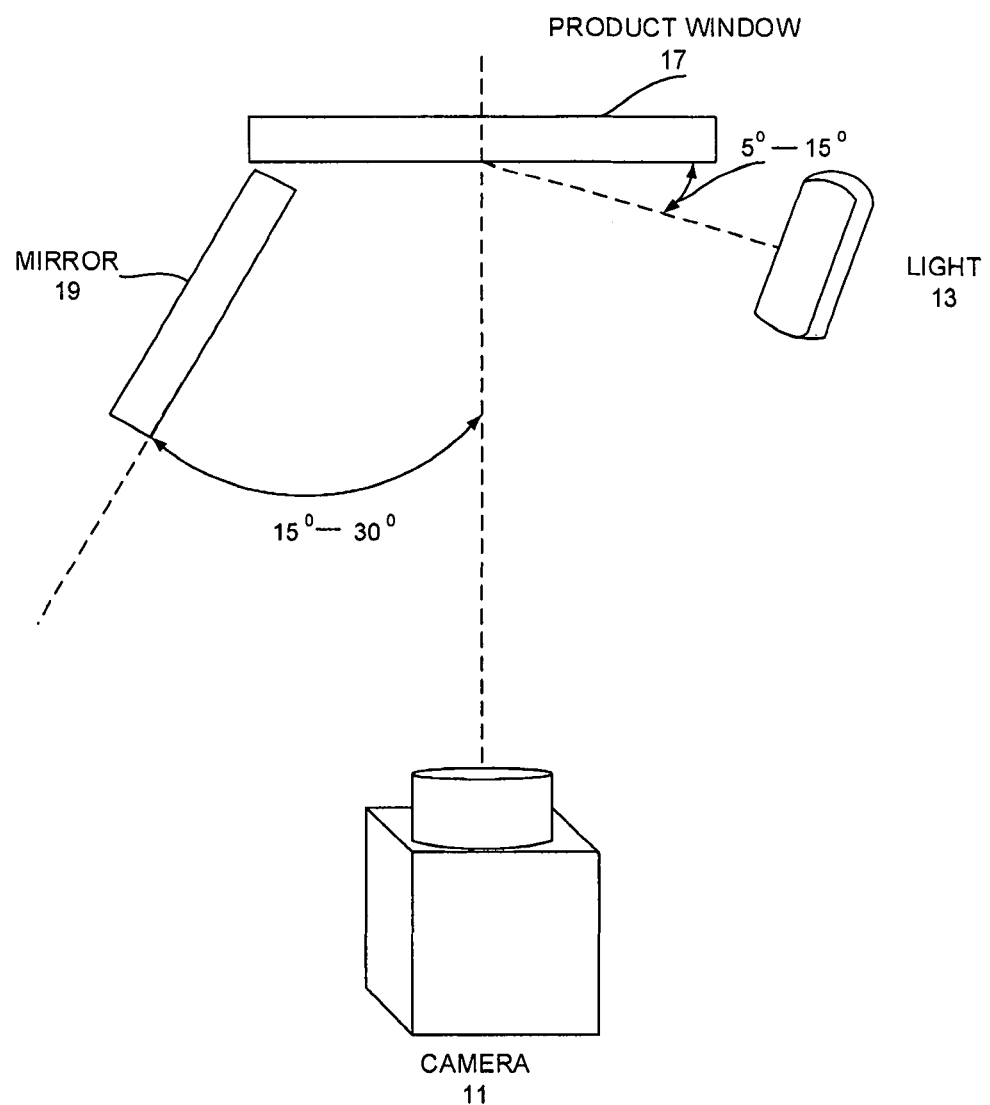
FIG. 2 is a schematic view showing an arrangement for determining the gloss of grain according to a second embodiment of the invention.

FIG. 2 is a schematic view showing an arrangement 1 for determining the gloss of grain 5 according to a second embodiment. In the embodiment according to FIG. 2 a window 17 is provided adjoining a channel 3 for conveying grain 5, which is aligned horizontally in FIG. 2. A mirror 19 is provided for reflecting light emitted by a light emitting device 13, cast through the window 17 on the grain 5 and reflected, respectively emitted, from there. The light is directed by the mirror 19 to an image acquiring device 11, which is realized as a digital camera in the second embodiment.

By providing the mirror 19 more flexibility with regard to positioning the light emitting device 13 relative to the image acquiring device 11 can be achieved. In the illustrated configuration the image acquiring device 11 gets a direct perpendicular view through the window 17 on the grain 5 and additionally captures the light from the light emitting device 13 via the grain 5 and the mirror 19. That allows a very sophisticated analysis of the gloss properties of the grain 5.

To achieve optimal assessment of specular gloss of the grain 5 the light emitting device 13 is orientated under an angle of 5° to 15° to the window 17 and the mirror 19 is aligned with its reflecting surface under an angle φ of 15° to 30° to the orientation of the image acquiring device 11.

We claim:

1. A method for measuring the gloss of grains, the method comprising:
    emitting a light beam to the surface of the grains by means of a light emitting device;
    aligning a light sensing device in a sensing position in relation to the light emitting device sensing the light beam of the light emitting device reflected by the surface of the grains in a direction of the light sensing device;
    capturing a photometric image of the surface of the grains by means of the light sensing device sensing the reflected light beam;
    assigning an intensity value to a plurality of image elements of the captured photometric image, wherein the photometric image is composed of the plurality of image elements;
    quantifying the reflected light beam in predefined ranges of intensities by means of a processing unit;
    cumulating the number of image elements having an intensity value within each of the predefined ranges;
    assigning a density value to each of the predefined ranges, each density value corresponding to a cumulated number of image elements within one of the predefined range;
    calculating a spread value for the density values of the predefined ranges by means of the processing unit, wherein the spread value is calculated by measuring a deviation of the density values of the predefined ranges; and
    assigning a quality surface measuring parameter to the captured photometric image, wherein the surface measuring parameter is a measure the spread value.

2. The method according to claim 1, further comprising generating an output signal based on the measured surface measuring parameter, wherein the output signal is useable for steering one or more process steps of a grain mill processing the grains.

3. The method according to claim 1, wherein the spread value is a measure of the dispersion/deviation of the density values of the predefined ranges of the captured image from an average image element density value.

4. The method according to claim 1, wherein the light sensing device is a photometer or a digital camera or a photometric sensor.

5. The method according to claim 1, further comprising fragmenting the photometric image in a plurality of image elements.

6. An arrangement for determining the gloss of grains, the arrangement comprising:
    a light emitting device emitting a light beam to the surface of the grains;
    a light sensing device in a sensing position in relation to the light emitting device for sensing the light beam of the light emitting device reflected by the surface of the grains in a direction of the light sensing device for capturing a photometric image of the surface of the grains by means of the light sensing device sensing the reflected light beam; and
    a process unit configured for:
        assigning an intensity value to a plurality of image elements of the captured photometric image, wherein the photometric image is composed of the plurality of image elements;
        defining predefined ranges of intensities;
        cumulating the number of image elements having an intensity value within each of the predefined ranges;
        assigning a density value to each of the predefined ranges, each density value corresponding to the cumulated number of image elements within one of the predefined ranges;
        calculating a deviation of the density values; and
        determining the degree of gloss of the grain based on the calculated deviation.

7. The arrangement of claim 6, comprising a channel for supplying grain in a conveying direction.

8. The arrangement of claim 7, wherein at a center of a shine measurement zone the direction to the light sensing device and the direction to the light emitting device comprise an angle of 130° to 160°.

9. The arrangement of claim 7, wherein the light sensing device is oriented at an angle of 15° to 30° to the conveying direction.

10. The arrangement of claim 7, wherein the light emitting device is oriented at an angle of 5° to 20° to the conveying direction.

11. The arrangement of claim 6, wherein a mirror is provided to reflect light emitted from the light emitting device from the grain sample to the light sensing device or to reflect light from the light emitting device to the grain sample.

12. The arrangement of claim 6, wherein the process unit comprises an output module for generating output signal based on the deviation, wherein the output signal is useable to steer a grain milling plant or an equipment of the grain milling plant.

* * * * *